United States Patent [19]
Finger et al.

[11] Patent Number: 5,272,301
[45] Date of Patent: Dec. 21, 1993

[54] THERMOSTATICALLY-CONTROLLED MICROWAVE USED FOR TREATMENT OF INTERNAL TISSUE OF THE EYE

[75] Inventors: Paul T. Finger, Manhasset, N.Y.; Fred Sterzer, Lawrence Township, Mercer County, N.J.

[73] Assignees: MMTC, Inc., Princeton, N.J.; North Shore University Hospital Research Corporation, Manhasset, N.Y.

[21] Appl. No.: 882,369

[22] Filed: May 6, 1992

Related U.S. Application Data

[63] Continuation-in-part of Ser. No. 691,720, Apr. 26, 1991, abandoned.

[51] Int. Cl.$^5$ ............................................... H05B 6/64
[52] U.S. Cl. ..................... 219/10.55 A; 219/10.55 B; 219/10.55 F; 219/10.55 M; 607/154; 607/116
[58] Field of Search ................. 219/10.55 A, 10.55 B, 219/10.55 M, 10.55 F; 73/355 EM, 359 R; 128/413, 736, 788, 800, 804, 784; 604/20; 606/3, 4, 11

[56] References Cited

U.S. PATENT DOCUMENTS

| | | | |
|---|---|---|---|
| 4,190,053 | 2/1980 | Sterzer | 128/399 |
| 4,204,549 | 5/1980 | Paglione | 128/784 |
| 4,271,848 | 6/1981 | Turner et al. | 128/804 |
| 4,282,887 | 8/1981 | Sterzer | 128/804 |
| 4,311,154 | 1/1982 | Sterzer et al. | 128/804 |
| 4,589,424 | 5/1986 | Vaguine | 219/10.55 F |
| 4,841,990 | 6/1989 | Kikuchi et al. | 219/10.55 F |

OTHER PUBLICATIONS

Microwave Cyclodestruction for Glaucoma in Rabbit Model Finger et al, Jul. 1991, vol. 109, pp. 1001-1004.
Microwave Thermotherapy for Glaucoma Moshfeghi et al, 1991, vol. 32(4):861.
Transscleral Microwave Cyclodestruction Finger et al, Oct. 1990, vol. 31, No. 10, pp. 2151-2155.
Microwave Conjunctivosclerocyclothermia Smith et al., 1989, vol. 30(3):380.

Primary Examiner—Bruce A. Reynolds
Assistant Examiner—Tu Hoang
Attorney, Agent, or Firm—George J. Seligsohn

[57] ABSTRACT

A miniaturized microwave applicator comprises a thin-wall metal dielectric-filled waveguide having a thermocouple preferably disposed in a groove in the surface of the dielectric radiating aperture of the waveguide when the aperture is placed in contact with a spot on the outer surface of the conjunctiva or sclera overlying the type of given internal tissue of the eye, such as the ciliary body or chorioretinal tissue, which has a relatively high water content compared to conjunctival or scleral eye tissue. This permits cyclodestruction of the ciliary body, as a treatment for glaucoma, by heat generated by absorbed microwave energy radiated thereto during a given time. It also permits microwave heating to repair a detached retina by chorioretinal scar formation. Damage due to overheating of the tissue is prevented by the thermocouple, which monitors the conjunctival or sclera surface temperature, being used to thermostatically control the microwave energy supplied to the waveguide in a manner that the conjunctival or scleral tissue temperature is maintained substantially constant at a value below that which would cause damage thereto. The desired operation is dependent on the fact that very little of the microwave energy is absorbed by the low-water-content conjunctival or scleral tissue as it passes therethrough, but is highly absorbed by the underlying high-water-content of the given internal tissue.

22 Claims, 4 Drawing Sheets

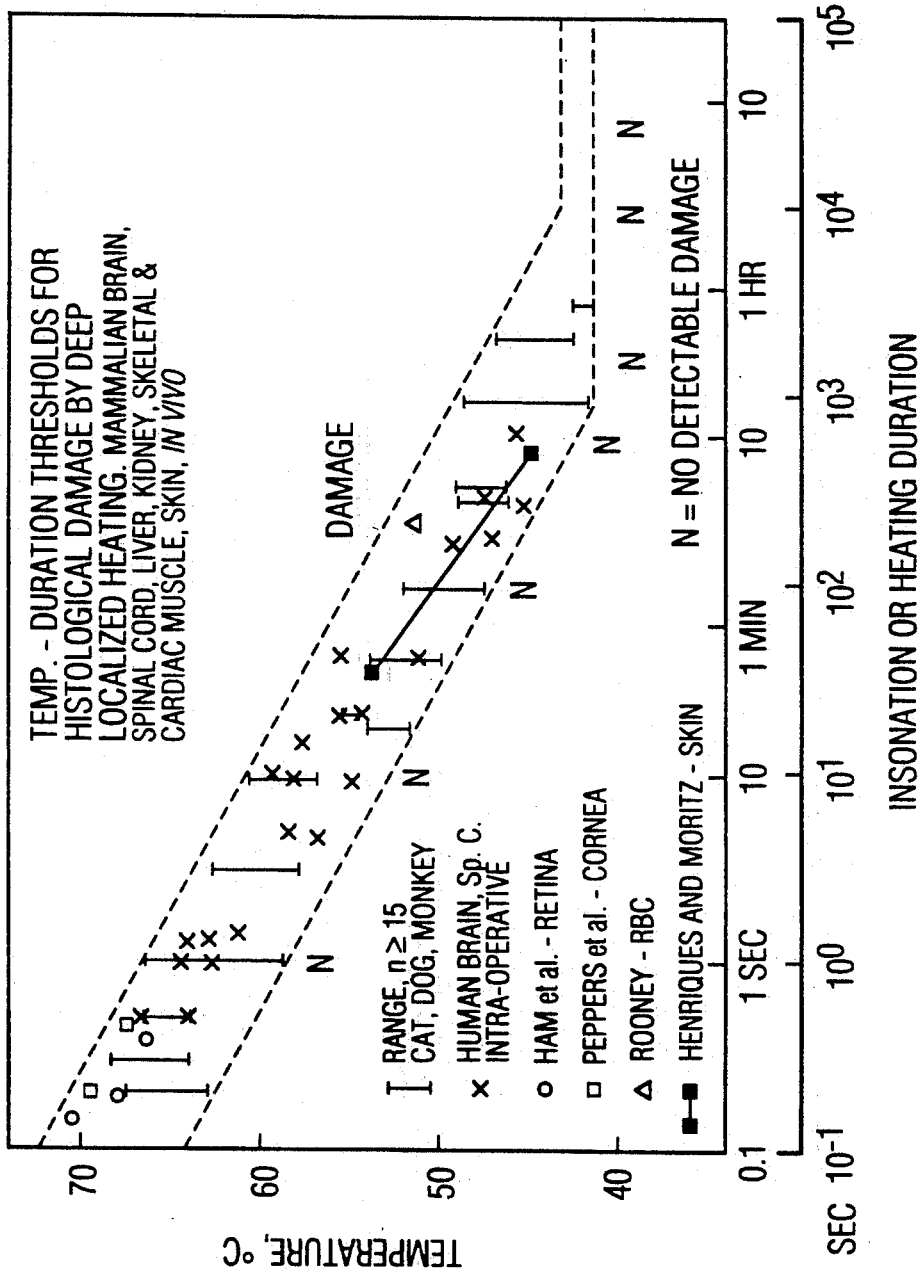

THERMOSTATICALLY-CONTROLLED MICROWAVE USED FOR TREATMENT OF INTERNAL TISSUE OF THE EYE

This is a continuation-in-part of application Ser. No. 07/691,720, filed on Apr. 26, 1991 now abandoned.

BACKGROUND

As known in the art, several different cyclodestruction procedures (i.e., procedures for destroying the ciliary body) have been developed or proposed for treating glaucoma. The clinical standard cyclodestruction procedure employs cryotherapy. Other known cyclodestruction procedures include therapeutic ultrasound and Neodymium:Yag cyclophotocoagulation. However, all of these known cyclodestruction procedures have demonstrated different negative tissue reactions.

Cryotherapy has been characterized by discomfort and edema, therapeutic sound by induced scleral changes, and Neodymium:Yag cyclophotocoagulation has been shown to cause characteristic spotlike conjunctival lesions. Other less specific morbidities have included corneal-scleral thinning, hyphema, cataract, vitritis, retinal detachment, cystoid macula edema, and hypotony. These potential complications have defined cyclodestruction procedures as a last treatment for refractory cases.

In addition to its use in treating glaucoma, cryotherapy is also used to repair retinal detachment by inducing chorioretinal scar formation to close retinal breaks, which chorioretinal scar formation creates adhesions between the retina and sclera. Prior to cryotherapy, radiofrequency diathermy was the standard method used for this purpose. However, radiofrequency diathermy has become less frequently utilized because (1) it requires scleral dissection or was associated with scleral necrosis, and (2) because cryotherapy, which is easier to use with indirect ophthalmoscopy, is associated with less scleral damage and does not require a scleral dissection. However, disadvantages attributed to cryotherapy lesions have been that they have less strength, therefore require more confluence of lesions, and may be associated with greater release of retinal pigment epithelial cells. While ophthalmic lasers have been used to repair retinal detachment, their use has been largely restricted to transpupillary or endoretinopexy applications.

SUMMARY OF THE INVENTION

The present invention is directed to a microwave procedure for treating a given internal tissue of the eye (e.g., such as cyclodestruction of the ciliary body as a treatment for glaucoma or inducing chorioretinal scar formation to repair retinal detachment), which given internal tissue has a relatively high water content compared to conjunctival or scleral eye tissue. In this microwave procedure, which avoids negative tissue reactions and minimizes potential complications, the microwaves are applied by a novel miniature microwave applicator placed in contact with a spot on the outer surface of the conjunctiva or sclera. While the shape of a miniature microwave applicator employed for cyclodestruction differs somewhat from the shape of a miniature microwave applicator employed for repairing retinal detachment, in both cases the miniature microwave applicator incorporates a thermocouple on its anterior radiating surface, so that the thermocouple also contacts the spot on the outer surface of the conjunctiva or sclera. The thermocouple thermostatically controls the output of the microwave generator energizing the applicator to ensure that the temperature of the conjunctiva or scleral tissue never rises to an unsafe level. Because conjunctiva or scleral tissue absorbs less microwave energy, while both ciliary-body tissue and chorioretinal tissue absorb more microwave energy, most of the applied applied microwave energy penetrates through the conjunctiva or sclera to, and is absorbed by, the underlying tissue. In the cyclodestruction case, the temperature of the ciliary body is raised to the point at which some cyclodestruction occurs. This process may be repeated at several separate spots of the conjunctiva or sclera to complete the microwave cyclodestruction procedure. In the retinal-detachment repair case, the temperature of the chorioretinal tissue is raised to the point at which chorioretinal scar formation occurs. Again, this process may be repeated at several separate spots of the conjunctiva or sclera to complete the microwave retinal-detachment repair. The microwave procedure of the present invention may be extended to the therapeutic treatment of any given internal eye tissue that has a high water content compared to conjunctiva or scleral tissue.

BRIEF DESCRIPTION OF THE DRAWINGS

FIG. 4 is a second chart useful in explaining the principles of the present invention.

DESCRIPTION OF THE PREFERRED EMBODIMENT

Figure 1:
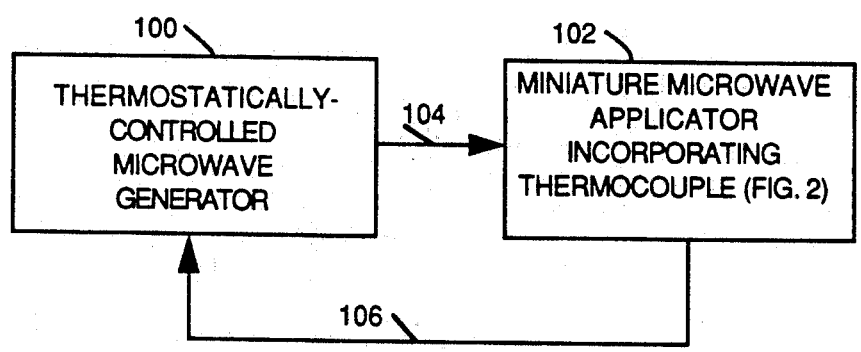
FIG. 1 is a functional block diagram showing the relationship between a miniature microwave applicator incorporating a thermocouple (which may take the form shown in FIG. 2) and a thermostatically-controlled microwave generator for energizing the applicator.

Referring to FIG. 1, the microwave output of thermostatically-controlled microwave generator 100 is applied as an input to miniature microwave applicator incorporating a thermocouple 102 (which may take the form shown in FIG. 2) over a suitable microwave transmission line 104. The thermocouple of applicator 102 generates a control signal having a value which is a function of the temperature at the microwave radiating aperture of applicator 102. This control signal, which is fed back to microwave generator 100 over connection 106 to thermostatically control microwave generator 100, prevents microwave energy from being forwarded from the output of microwave generator 100 over transmission line 104 to the input of applicator 102 whenever the temperature of the thermocouple rises to a certain preselected temperature.

Figure 2:
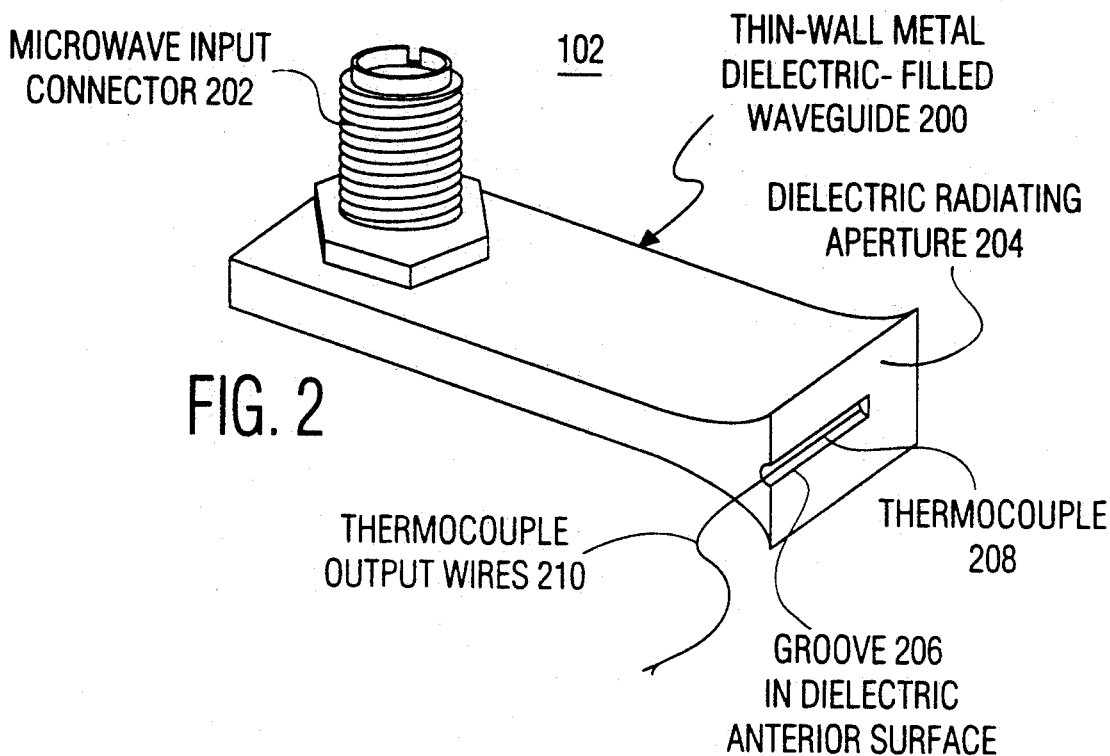
FIG. 2 illustrates the physical form of a preferred embodiment of the miniature microwave applicator incorporating a thermocouple that is used for microwave cyclodestruction.

Referring to FIG. 2, applicator 102 comprises thin-wall metal dielectric-filled waveguide 200. In practice, waveguide 200 is fabricated from a block of ceramic material that exhibits a high dielectric constant (e.g., 85) that is machined to the proper size and shape. The longitudinal surface of this properly sized and shaped ceramic material is first electrolessly plated with metal and then electroplated with metal to produce the thin metal wall of waveguide 200. More specifically, the length of waveguide 200 is preferably about one inch; the width of waveguide 200 is preferably about 0.2 inch (i.e., 200 mils); and the thickness of waveguide 200 preferably tapers from about 0.1 inch (i.e., 100 mils) at its posterior end, to which microwave input connector 202 is attached, to about 0.15 inch (i.e., 150 mils) at its anterior end, which forms dielectric radiating aperture 204. Thus, the area of dielectric radiating aperture 204 is quite small, being only 0.03 square inch.

As shown in FIG. 2, the dielectric anterior surface, which is preferably flat, has a groove 206 machined therein in which thermocouple 208 is fixedly secured substantially at the center thereof. The thickness of the thermocouple is preferably sufficient to protrude very slightly from the flat dielectric anterior surface. Thermocouple output wires 210, connected to thermocouple 208, extend through the length of groove 206 to the outside of waveguide 200, as shown in FIG. 2. Thermocouple output wires 210 constitute feedback connection 106 of FIG. 1.

The therapeutic purpose of applicator 102 in the treatment of glaucoma is to apply sufficient microwave energy to the ciliary body to effect cyclodestruction without creating collateral eye damage. This is accomplished by first positioning 0.03 square inch dielectric radiating aperture 204 in contact with the anterior surface of applicator 102 in contact with a 0.03 square inch spot on the outer surface of the sclera which overlies the ciliary body (e.g., a spot displaced about 2 millimeters beyond the outer edge of the iris). This inherently places thermocouple 208 in contact with this spot. The applicator is energized with microwave energy having a frequency (e.g. 5,000 to 6,000 MHz) which readily penetrates the thickness of the scleral tissue with little absorption and reaches a corresponding spot of the underlying ciliary body, where it is readily absorbed. The reason for this is shown by the FIG. 3 chart, which will be discussed below.

The microwave energy is applied to the spot for a given time (e.g., one minute) which is a sufficient time for the irradiated spot of the ciliary body to be heated to a high enough temperature to cause cyclodestruction, while the sclera itself is never heated enough to raise its temperature sufficiently high to result in damage thereto. (The FIG. 4 chart, discussed in more detail below, indicates the the relationship between temperature and time of heating duration that results in damage to different types of mammalian tissue.) In any event, the thermostatic control of microwave generator 100 is set so that the radiated microwave energy is cut off whenever the temperature of thermocouple 208 rises to a preselected therapeutic temperature which is below the temperature at which scleral damage occurs. Thus, the continuous monitoring of sclera-spot surface temperature by thermocouple 208 maintains the temperature substantially constant at the therapeutic temperature and also ensures that the operation is fail-safe.

In order to complete the microwave cyclodestruction procedure, the above-described process is applied sequentially to each of several (e.g., five) displaced spots on the outer surface of the sclera. More specifically, after the above-described process with respect to one of the several displaced spots is completed, the applicator is displaced by about the width of applicator 102 (200 mils) to another similar scleral spot overlying the ciliary body. Thus, the resulting several displaced spots tend to lie on the circumference of a circle having a radius about 2 millimeters larger than that of the iris.

Figure 3:
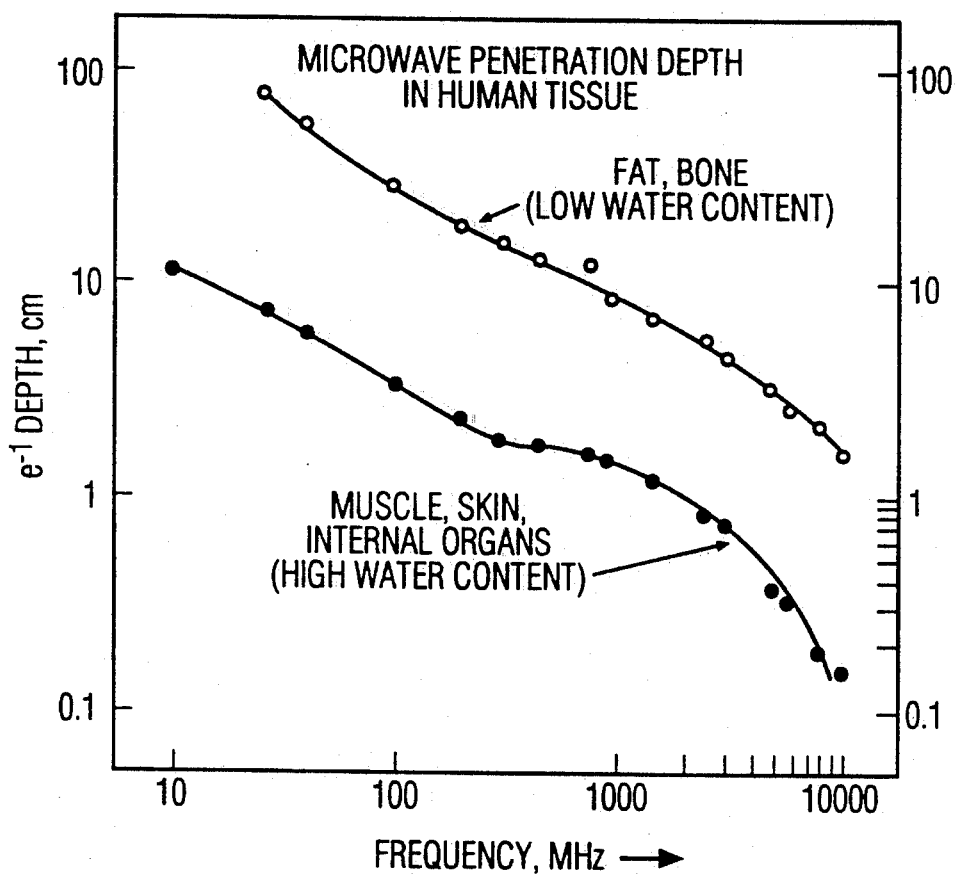
FIG. 3 is a first chart useful in explaining the principles of the present invention.

Referring to the FIG. 3 chart, there is shown the penetration depth as a function of frequency at which $1/e$ (where e is the base of natural logarithm) of incident microwave energy is absorbed by low-water-content human tissue and by high-water-content human tissue, respectively. It is apparent from this chart that low-water-content human tissue is much less microwave absorbent than high-water-content human tissue. Scleral human tissue is low-water-content human tissue and ciliary-body tissue is high-water-content human tissue. Thus, most of the applied microwave energy merely passes through the thickness of the scleral tissue to be then highly absorbed by the underlying ciliary-body tissue, thereby preferentially heating the underlying ciliary-body tissue.

Referring to the FIG. 4 chart, there is shown temperature-time duration thresholds for damage to occur in different types of mammalian tissue. As indicated by the wide band of the FIG. 4 chart, for a given heating duration some types of tissue (e.g., corneal tissue) are damaged substantially less than others. It has been found that both corneal and scleral tissue are not damaged by, and tolerate well, being heated to a temperature up to about 50° C. for at least one minute. Therefore, the aforesaid fail-safe thermostatically-controlled therapeutic temperature for a heating duration of scleral tissue for one minute certainly may be set at 50° C., and perhaps even somewhat higher.

Returning to FIG. 2, the high dielectric constant of the dielectric filling of waveguide 200 of applicator 102 serves two important purposes. First, by reducing the microwave wavelength traveling therein for a given microwave frequency, the size of applicator 102 for transporting that given microwave frequency may be reduced (i.e., miniaturized). Second, the high dielectric constant of the dielectric filling of waveguide 200 more nearly matches the high dielectric constant of the high-water content ciliary body, and, therefore, enhances microwave power transfer from dielectric radiating aperture 204 to the ciliary body. Further, for microwave power transfer purposes, the impedance at the microwave input to applicator 102 at the posterior end of waveguide 200 should closely match that presented by transmission line 104, and the impedance at the microwave output from applicator 102 at dielectric radiating aperture 204 (located at the anterior end of waveguide 200) should closely match that presented by the scleral tissue with which it is in contact. The proper impedance matching at both the posterior and anterior ends of waveguide 200 is achieved by the above-discussed tapering of the thickness of waveguide 200 from 100 mils at its posterior end to 150 mils at its anterior end.

The above-described controlled microwave cyclodestruction procedure has been tested experimentally in the treatment of induced glaucoma in the eyes of rabbits. Microwave induced cyclodestruction was successful in reducing the intraocular pressure in all treated glaucomatous eyes for a 4 week duration. Two additional glaucomatous eyes were left untreated, served as controls, and were noted to have persistently elevated intraocular pressures. Then 6 additional eyes were subjected to an equivalent treatment (50° C.×1 min.×5 applications) which resulted in approximately 180° of heat treatment just posterior to the corneal-scleral limbus. These specimens were evaluated by light microscopy at time 0, 24 hours, and at 7 days after treatment.

Clinical and histopathologic evaluations suggested that microwave thermotherapy (delivered under thermometry control) allowed for chorioretinal/ciliary body destruction which resulted in reductions of intraocular pressure in glaucomatous eyes.

Generalizing from the above-described microwave cyclodestruction process, it can be seen that the advantages of microwaves are that tissues with relatively low water content (e.g. conjunctiva and sclera) absorb less energy than tissues with relatively high water content (e.g. choroid, retina, vitreous); that energy deposition into tissue can be modulated by microwave frequency selection, and that microwave technology and components are relatively inexpensive. This permits the microwave principles of the present invention to be used for other ophthalmological therapeutic purposes, including the repair of retinal detachment by inducing chorioretinal scar formation to close retinal breaks.

Figure 5:
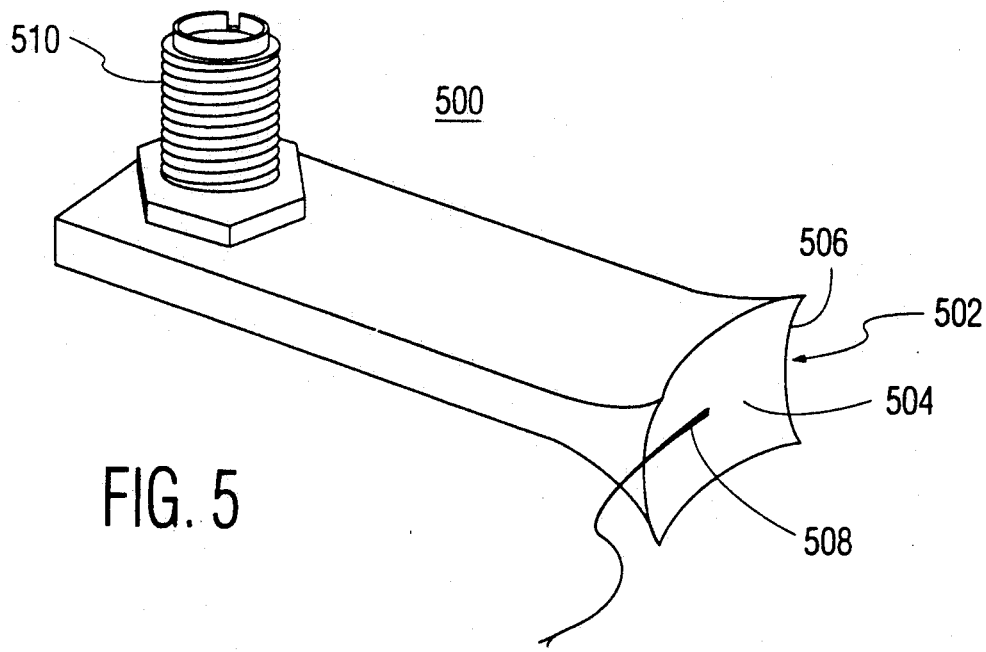
FIG. 5 illustrates the physical form of a preferred embodiment of the miniature microwave applicator incorporating a thermocouple that is used for microwave chorioretinal repair.

In this regard, reference is made to FIG. 5, which shows the physical form of miniature microwave applicator 500, which is substituted for miniature microwave applicator 102 of FIGS. 1 and 2. The design of miniature microwave applicator 500, which is used for microwave chorioretinal repair, rather than for cyclodestruction, differs in certain respects from the design of miniature microwave applicator 102, described above. While applicator 500, like applicator 102, comprises a thin-wall metal dielectric-filled waveguide, the shape of dielectric radiating aperture 502 in the anterior surface of applicator 500 is substantially different from the shape of dielectric radiating aperture 204 in the anterior surface of applicator 102. Specifically, as shown in FIG. 5, the anterior surface comprising dielectric radiating aperture 502 includes rectangular dish-shaped portion 504 surrounded by flat rectangular frame portion 506, rather than being an entirely flat surface like the anterior surface comprising dielectric radiating aperture 204. However, like the anterior surface of applicator 102, the anterior surface of applicator 500 preferably includes a groove 508 machined therein in which a thermocouple may be fixedly secured substantially at the center thereof, although the thermocouple could be fixedly attached directly to the anterior surface of applicator 500. The shape of microwave applicator is designed to mimic the shape and function of a standard scleral depressor.

In more detail, applicator 500 is constructed as rectangular silver waveguide filled with a low-loss, high dielectric-constant ceramic. Its posterior end is closed with a metallic short circuit and dielectric radiating aperture 502 at its anterior end measures 2.8×5.6 mm. Microwave power is introduced into the waveguide by a transition made of semi-rigid coaxial cable with a standard subminiature (SMA) connector mounted on its distal end. A 6.8 GHz thermostatically-controlled microwave generator, similar to generator 100, and an amplifier (not shown) provide the required microwave power.

Microwave applicator 500 was employed experimentally to deliver microwaves at a frequency of 6.8 GHz for a time interval of 10 seconds through the conjunctiva and sclera of the eyes of each of 12 rabbits. A computer program driven thermometry system, that was responsive to the temperature measured by a copper-constantan thermocouple thermometer (from Physitemp, Clifton, N.J., U.S.A.), controlled the amount of microwave energy supplied to any particular one of the 12 rabbit's eye during a 10-second time interval, and, hence, the measured external eye temperature at the end of the 10-second time interval. Respective conjunctival temperatures of 65, 57, 53, 52 and 51 degrees C. were obtained by the use of this computer program. While significant damage to the conjunctiva or sclera occurred at the 65° C. temperature, it was found that at the respective lower temperatures of 51° C. or 52° C., reached after a dose of microwave energy (i.e., a 10-second application of a certain amount of microwave power), was sufficient to produce chorioretinal scar formation without scleral or conjunctival toxicity. At these temperatures, there were no complications which might preclude clinical application of microwave applicator 500 for the repair of retinal detachment by inducing chorioretinal scar formation to close retinal breaks.

In comparison to other methods of heat induced chorioretinal scar formation, the most important advantage of the microwave heat delivery system described above, is the use of thermocouple thermometry to control the temperature of treatment.

While the ophthalmological therapeutic uses of miniature microwave applicators described herein have been confined to cyclodestruction and the repair of retinal detachment, the ability of such microwave applicators to controllably heat high-water-content internal eye tissue through overlying low water-content external eye tissue may have other ophthalmological therapeutic uses.

What is claimed is:

1. A method of therapeutically treating given internal eye tissue of a type which has a relatively high water content compared to its conjunctival or scleral eye tissue, wherein said conjunctival or scleral eye tissue would undergo damage when heated to a first temperature; said method comprising the steps of:
   (a) supplying microwave energy to said given internal eye tissue through a given spot on an outer surface of conjunctival or scleral tissue which overlies said given internal eye tissue;
   (b) continuously monitoring temperature value of said given spot; and
   (c) thermostatically controlling the supply of said microwave energy in accordance with said continuously-monitoring temperature value to maintain the temperature value of said given spot substantially constant at a preselected value which is below said first temperature, while permitting a temperature of said given internal eye tissue itself to be raised to a given second temperature substantially higher than said first temperature for a given time by said microwave energy supplied thereto, said given second temperature and said given time being sufficient to effect therapeutic treatment of said given internal eye tissue.

2. The method defined in claim 1, wherein said conjunctival or scleral tissue has a certain thickness, and step (a) comprises the step of:
   (d) supplying microwave energy to said given spot having a frequency value which penetrates the certain thickness of said conjunctival or scleral tissue and reaches a corresponding spot of underlying given internal eye tissue, wherein, due to the relatively high water content of said given internal eye tissue compared to said conjunctival or scleral eye tissue, a relatively large fraction of said microwave energy of said frequency value is absorbed by said given internal eye tissue compared to the fraction of said microwave energy of said frequency value absorbed by said conjunctival or scleral eye tissue.

3. The method defined in claim 2, wherein said frequency value is in a range of 5,000 to 7,000 MHz.

4. The method defined in claim 1, wherein said given internal eye tissue is ciliary-body tissue, and said method is a method for employing microwave heating to treat glaucoma by cyclodestruction.

5. The method defined in claim 4, wherein said given time is at least one minute.

6. The method defined in claim 1, wherein step (a) comprises the step of:
   (d) supplying microwave energy to a substantially 0.03 square inch given spot situated on an outer surface of scleral tissue and substantially 2 millimeters beyond an eye's iris' outer edge.

7. The method defined in claim 4, wherein step (a) comprises the step of:
   (d) supplying microwave energy in sequence to ciliary-body tissue through each of a plurality of separate given spots on the outer surface of scleral tissue all of which overly said ciliary-body tissue.

8. The method defined in claim 7, wherein step (d) comprises the step of:
   (d) supplying microwave energy to each of a plurality of displaced, substantially 0.03 square-inch, given spots situated on the outer surface of scleral tissue and substantially 2 millimeters beyond an eye's iris' outer edge, the displacement between adjacent given spots being substantially 200 mils.

9. The method defined in claim 1, wherein said preselected value of said temperature of said given spot is no greater than 55° C.

10. The method defined in claim 1, wherein said given internal eye tissue is chorioretinal tissue, and said method is a method for repairing retinal detachment by employing microwave heating to induce chorioretinal scar formation to close retinal breaks.

11. A miniaturized microwave applicator for use in non-invasive therapeutic treatment of given internal eye tissue of a type which has a relatively high water content compared to its conjunctival or scleral eye tissue; said applicator comprising a waveguide responsive to a microwave input of a given frequency supplied thereto at its posterior end for radiating microwave energy of said given frequency from a radiating surface of an aperture situated at its anterior end; wherein:
   said waveguide includes a thin metal wall filled with solid dielectric material having a given dielectric constant that extends between said anterior and posterior ends and has a given first area at said radiating surface of said aperture, whereby said radiating surface of said aperture is a dielectric radiating surface;
   said dielectric radiating surface of said aperture adapted to have a thermocouple fixedly attached thereto;
   said given dielectric constant of said solid dielectric material has a value that at least approximates the value of water's dielectric constant; and
   said given first area has a first size that permits said dielectric radiating surface of said aperture to contact only a given spot of conjunctival or scleral tissue of an eye that overlies substantially solely said given internal eye tissue of said eye.

12. The microwave applicator defined in claim 11, wherein:
   said solid dielectric material consists of a ceramic block having said given dielectric constant.

13. The microwave applicator defined in claim 12, wherein:
   said given dielectric constant has a value of about 85.

14. The microwave applicator defined in claim 12, wherein:
   said thin metal wall comprises a metal plating on a surface of said ceramic block.

15. The microwave applicator defined in claim 11, wherein:
   the size of said given area is substantially in a range between 0.02 and 0.03 square inch.

16. The microwave applicator defined in claim 11, wherein said microwave input is supplied to said posterior end of said waveguide by transmission means exhibiting a predetermined characteristic impedance; and wherein:
   said thin metal wall filled with solid dielectric material has a second given area of a size at the posterior end of said waveguide to provide said waveguide with an input impedance that substantially matches said predetermined characteristic impedance exhibited by said transmission means.

17. The microwave applicator defined in claim 16, wherein:
   said second given area's size is different from that of said first size of said given first area at said radiating surface of said aperture, and a thin metal wall's cross section, which is filled with solid dielectric material, tapers in size between said second and first given areas.

18. The microwave applicator defined in claim 17, wherein:
   said first-mentioned given area has a width of substantially 200 mil and a thickness of substantially 150 mil; and
   said second given area has a width of substantially 200 mil and a thickness of substantially 100 mil.

19. The microwave applicator defined in claim 11, further comprising:
   a thermocouple fixedly attached to said dielectric radiating surface of said aperture for measuring temperature; and
   thermocouple output wires adapted to deliver a signal indicative of the temperature of said thermocouple to external means for thermostatically controlling said microwave input supplied at said posterior end of said waveguide in order to prevent said thermocouple temperature from ever exceeding a temperature having a preselected value that is below that which would result in damage to conjunctival or scleral tissue;
   whereby microwave energy radiated from said dielectric aperture of said applicator is used to effect therapeutic treatment of said given internal eye tissue by positioning said dielectric aperture in contact with said given spot on the outer surface of conjunctival or scleral tissue which overlies said given internal eye tissue, thereby also situating said thermocouple in contact with said given spot.

20. The microwave applicator defined in claim 19, wherein:
   said dielectric radiating surface of said aperture includes a groove therein; and said thermocouple is situated within said surface groove in said dielectric radiating surface of said aperture.

21. The microwave applicator defined in claim 11, wherein:
said radiating surface has a flat shape; and
said microwave applicator is for use in the treatment of glaucoma by cyclodestruction.

22. The microwave applicator defined in claim 11, wherein:
said radiating surface has a dish-shape to mimic a shape and function of a scleral depressor; and
said microwave applicator is for use in the repair of retinal detachment by inducing chorioretinal scar formation to close retinal breaks.

* * * * *